(12) United States Patent
Miyamoto (10) Patent No.: US 9,396,535 B2
(45) Date of Patent: Jul. 19, 2016

(54) IMAGE PROCESSING APPARATUS, IMAGE PROCESSING METHOD AND STORAGE MEDIUM TO GENERATE SUBTRACTION IMAGE

(71) Applicant: CANON KABUSHIKI KAISHA, Tokyo (JP)

(72) Inventor: Hideaki Miyamoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 80 days.

(21) Appl. No.: 13/867,266

(22) Filed: Apr. 22, 2013

(65) Prior Publication Data

US 2013/0294674 A1 Nov. 7, 2013

(30) Foreign Application Priority Data

May 7, 2012 (JP) .................................. 2012-106311

(51) Int. Cl.
*G06K 9/00* (2006.01)
*G06T 7/00* (2006.01)
*A61B 6/00* (2006.01)

(52) U.S. Cl.
CPC ............. *G06T 7/0014* (2013.01); *A61B 6/5241* (2013.01); *G06T 7/0012* (2013.01); *A61B 6/481* (2013.01); *A61B 6/504* (2013.01); *G06T 2207/10121* (2013.01); *G06T 2207/30021* (2013.01); *G06T 2207/30101* (2013.01); *G06T 2207/30168* (2013.01)

(58) Field of Classification Search
None
See application file for complete search history.

(56) References Cited

U.S. PATENT DOCUMENTS

| | | | |
|---|---|---|---|
| 6,195,450 B1 * | 2/2001 | Qian et al. | 382/130 |
| 2003/0048935 A1 * | 3/2003 | Keren | A61B 6/504 382/130 |
| 2003/0169912 A1 * | 9/2003 | Shinbata | 382/131 |
| 2005/0089143 A1 * | 4/2005 | Nakano et al. | 378/98.12 |
| 2008/0287784 A1 | 11/2008 | Ohta et al. | 600/431 |
| 2009/0046911 A1 * | 2/2009 | Inoue | A61B 6/504 382/130 |
| 2009/0279663 A1 | 11/2009 | Miyamoto | 378/62 |
| 2011/0226956 A1 | 9/2011 | Miyamoto | 250/354.1 |
| 2011/0293164 A1 | 12/2011 | Sato et al. | 382/132 |

FOREIGN PATENT DOCUMENTS

CN 1382421 A 12/2002
CN 102258379 A 11/2011

(Continued)

OTHER PUBLICATIONS

R. Johnson et al., "Exploring the Potential for Touchless Interaction in Image-Guided Interventional Radiology", *CHI 2100—Session: Doctor-Patient Care* (XP055073761 ) (May 7, 2011).

(Continued)

*Primary Examiner* — Hadi Akhavannik
(74) *Attorney, Agent, or Firm* — Fitzpatrick, Cella, Harper & Scinto (57) ABSTRACT

An image processing apparatus includes: a subtraction unit that generates subtraction images constituted by a plurality of frames from X-ray images of an object acquired before and after injecting a radiopaque dye; an evaluation unit that calculates evaluation values indicating states of the injection of the radiopaque dye for the frames constituting the subtraction images; and a selection unit that selects at least one of the frames constituting the subtraction images using the evaluation values and outputs the selected frame as a reference image.

18 Claims, 4 Drawing Sheets

(56) References Cited

FOREIGN PATENT DOCUMENTS

| | | |
|---|---|---|
| JP | 01-221142 | 9/1989 |
| JP | 2005-087633 | 4/2005 |
| JP | 2010-240156 | 10/2010 |
| JP | 2012-065792 | 4/2012 |
| WO | 2011/074655 A1 | 6/2011 |
| WO | 2011/074657 A1 | 6/2011 |
| WO | 2012/029459 A1 | 3/2012 |

OTHER PUBLICATIONS

"Spectum E-5000 Cardiac Catheterization Lab" ( XP055073858 ; no author identified) (Feb. 13, 2011).

EESR issued Aug. 12, 2013 in counterpart EPA 13163985.8.

Office Action issued on Oct. 10, 2014 in counterpart PRC patent application 201310163992.5, with translation.

* cited by examiner

IMAGE PROCESSING APPARATUS, IMAGE PROCESSING METHOD AND STORAGE MEDIUM TO GENERATE SUBTRACTION IMAGE

BACKGROUND OF THE INVENTION

1. Field of the Invention

The present invention relates to an image processing apparatus, an image processing method and a storage medium. In particular, the present invention relates to an image processing technique for selecting an image suitable for use in diagnosis and surgery from a plurality of X-ray digital subtraction angiography images.

2. Description of the Related Art

Recent advancement in digital technology has made it common to apply digital processing to images in the medical field. In place of the conventional X-ray imaging that uses films for X-ray diagnosis, two-dimensional X-ray sensors that output X-ray images as digital images have become widespread. The application of digital image processing to digital images output from the two-dimensional X-ray sensors comes in a broad range.

One example of suitable application of such digital image processing is digital subtraction angiography (DSA) processing for acquiring a DSA image. A DSA image is a subtraction image acquired as follows. Images are acquired before and after a radiopaque dye is injected into an object. The result of subtracting the image acquired before the injection of the radiopaque dye (hereinafter, "mask image") from the image acquired after the injection of the radiopaque dye (hereinafter, "live image") is a subtraction image. A DSA image not only keeps a blood vessel region, which is a region of interest used in diagnosis, as a region exhibiting a difference between the images acquired before and after the injection of the radiopaque dye, but also removes all unnecessary region other than the region exhibiting the difference as a background region and shows the background region in a uniform fashion. That is to say, in a DSA image, a region of blood vessels filled with the radiopaque dye, which becomes less visible in a live image due to obstruction by the background region, clearly appears as a subtraction image. Such a DSA image is commonly used in vascular interventional radiology (IVR). Vascular IVR is a technique to insert a catheter into a target organ in a body while checking X-ray fluoroscopy images.

Regarding DSA processing, for example, Japanese Patent Laid-Open No. 1-221142 discloses the invention of an X-ray image processing apparatus suitable for acquiring orientation images that make it easy to understand how the blood vessels are arranged during surgery and the like.

Normally, X-ray fluoroscopy images cannot show blood vessels with high X-ray transmittance. To show such blood vessels, a radiopaque dye is administered. However, in vascular IVR, if the radiopaque dye is injected continuously until a catheter reaches a target organ, then a large dosage of radiopaque dye would be ultimately administered, which increases the burden on a patient. In view of this, in general vascular IVR, a predetermined dosage of radiopaque dye is administered prior to fluoroscopy, and images are captured successively thereafter. By subtracting a pre-angiography image from successive post-angiography images, subtraction images are acquired as moving images that serve as DSA moving images. From the DSA moving images, a frame that clearly shows blood vessels through which the catheter should be advanced is selected (hereinafter, "reference image"). The reference image is displayed on a second monitor that is different from a main monitor for displaying fluoroscopic images. The reference image is used as a guide to advance the catheter during fluoroscopy.

In general vascular IVR, the following operations are carried out repeatedly until the catheter reaches a target organ: a catheter operation via fluoroscopy, successive imaging under administration of a radiopaque dye, generation of DSA moving images from acquired images, and selection of a frame used as a reference image. The administered dosage of radiopaque dye can be suppressed by using a reference image acquired prior to fluoroscopy instead of operating the catheter under administration of the radiopaque dye during fluoroscopy.

Conventionally, in order to select a reference image from DSA moving images, a technician searches for an optimal frame through visual examination by, for example, reproducing, frame-forwarding and frame-reversing the DSA moving images. In general vascular IVR, the catheter does not reach a target organ by a catheter operation involving a single generation of DSA moving images and a single fluoroscopy. That is to say, generation of DSA moving images and selection of a reference image are repeated multiple times in accordance with the state of catheter insertion. Therefore, selection of a reference image is a very troublesome operation for the technician and could increase the amount of time required for the treatment.

In view of the above problems, the present invention provides an image processing technique that enables reduction in the effort required to select a reference image to be displayed on a second monitor during vascular IVR.

SUMMARY OF THE INVENTION

According to one aspect of the present invention, there is provided an image processing apparatus comprising: a subtraction unit configured to generate digital subtraction angiography images constituted by a plurality of frames from X-ray images of an object acquired before and after injecting a radiopaque dye into the object; an evaluation unit configured to calculate evaluation values indicating the state of the injection of the radiopaque dye for each of the frames constituting the digital subtraction angiography images; and a selection unit configured to select at least one of digital subtraction angiography image using the evaluation values and to output the selected, at least one, digital subtraction angiography image as a reference image.

According to another aspect of the present invention, there is provided an image processing method for an image processing apparatus, the method comprising: a subtraction step of generating digital subtraction angiography images constituted by a plurality of frames from X-ray images of an object acquired before and after injecting a radiopaque dye into the object; an evaluation step of calculating evaluation values indicating the states of the injection of the radiopaque dye for each of the frames constituting the digital subtraction angiography images; and a selection step of selecting at least one digital subtraction angiography image using the evaluation values and outputting the selected, at least one, digital subtraction angiography image as a reference image.

The present invention enables reduction in the effort required to select a reference image to be displayed on a second monitor during vascular IVR.

Further features of the present invention will become apparent from the following description of exemplary embodiments (with reference to the attached drawings).

Each of the embodiments of the present invention described below can be implemented solely or as a combination of a plurality of the embodiments or features thereof where necessary or where the combination of elements or features from individual embodiments in a single embodiment is beneficial.

DESCRIPTION OF THE EMBODIMENTS

The following describes one example of embodiments of the present invention with reference to the drawings.

First Embodiment

A description is now given of an image processing apparatus according to the first embodiment of the present invention (hereinafter, "X-ray image processing apparatus 100") with reference to FIG. 1. The X-ray image processing apparatus 100 includes an X-ray generation unit 101, a two-dimensional X-ray sensor 104, a preprocessing unit 105, an image storage unit 106, an inter-image subtraction unit 107, an evaluation unit 108, a reference image selection unit 109, and an image display unit 110.

The X-ray generation unit 101 can generate X-ray pulses (X-rays) at 3 to 30 pulses per second. The two-dimensional X-ray sensor 104 can capture moving images. More specifically, the two-dimensional X-ray sensor 104 receives X-rays 103 that have been transmitted through an object 102, and captures moving images synchronized with the X-ray pulses. The two-dimensional X-ray sensor 104 also functions as an imaging unit that captures moving images of the object 102 illuminated with the X-rays.

The preprocessing unit 105 preprocesses frames of the moving images output from the two-dimensional X-ray sensor 104. The image storage unit 106 stores at least one of the frames of the moving images preprocessed by the preprocessing unit 105 as a mask image acquired before injecting a radiopaque dye. Note that a frame stored as a mask image is, for example, a frame that is acquired immediately after an operation of capturing the moving images is started, or a frame that is automatically acquired immediately before the injection of a radiopaque dye by detecting the injection of the radiopaque dye from the moving images. Alternatively, a frame stored as a mask image may be a frame that is selected by an operator designating a storage timing when starting the injection of the radiopaque dye. Alternatively, a frame used as a mask image may be selected as appropriate from a plurality of frames stored in the image storage unit 106, or may be acquired by compositing a plurality of frames.

The inter-image subtraction unit 107 generates images composed of a plurality of frames from X-ray images of the object acquired before and after the injection of the radiopaque dye. More specifically, the inter-image subtraction unit 107 generates subtraction images by subtracting the mask image stored in the image storage unit 106 from live images, which are images (frames) that are acquired after the injection of the radiopaque dye and are output from the preprocessing unit 105, and outputs the subtraction images as frames of DSA moving images.

The evaluation unit 108 calculates, from the frames of the DSA moving images output from the inter-image subtraction unit 107, evaluation values indicating the states of the injection of the radiopaque dye for the frames, and outputs the evaluation values.

The reference image selection unit 109 selects at least one of the frames of the DSA moving images based on the evaluation values for the frames output from the evaluation unit 108, and outputs the selected frame as a reference image.

The image display unit 110 displays the reference image output from the reference image selection unit 109. In the case where a plurality of frames have been selected as reference images, the image display unit 110 can reproduce the reference images one by one in a loop at a predetermined frame rate. The reference image selection unit 109 may output and store a reference image to a storage unit not shown in the figures. In this case, the image display unit 110 can display the reference image stored in the storage unit.

Figure 2:
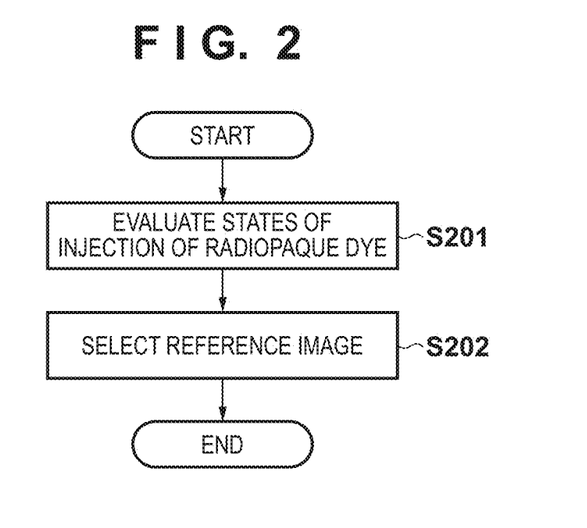
FIG. 2 illustrates a flow of an image processing method according to an embodiment.

With reference to a flowchart of FIG. 2, the following describes the operations of the evaluation unit 108 and the image display unit 110 that represent characteristic configurations of the present embodiment in connection with the X-ray image processing apparatus 100 configured in the above manner.

In step S201, the inter-image subtraction unit 107 outputs the frames of the DSA moving images to the evaluation unit 108, and the evaluation unit 108 outputs the evaluation values calculated by evaluating the states of the injection of the radiopaque dye for the frames of the DSA moving images. The states of the injection of the radiopaque dye may be evaluated using various methods. Below, an evaluation method based on the area of a blood vessel region in each frame (DSA image) of the DSA moving images is explained as one example.

Figure 3:
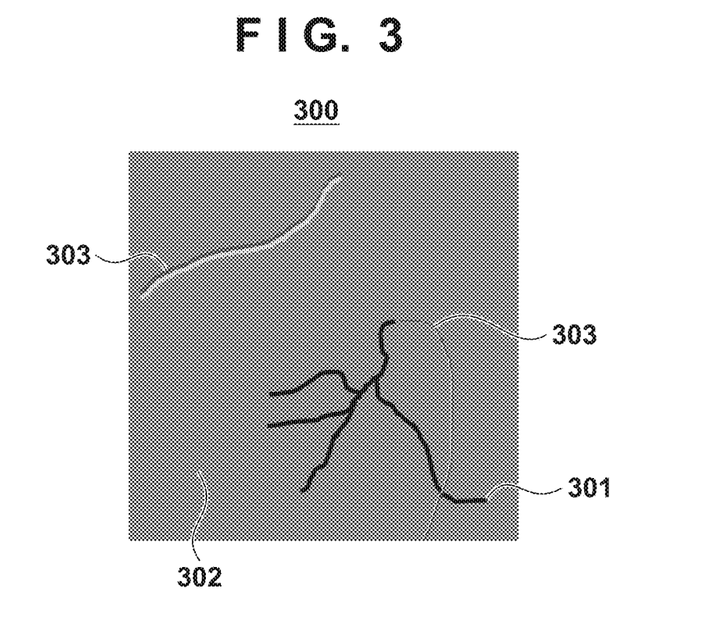
FIG. 3 schematically illustrates a subtraction image.

FIG. 3 is a schematic diagram illustrating a subtraction image acquired by subtracting a mask image from a live image. The subtraction image illustrated in FIG. 3 has pixel values of −1.0 to 1.0. Pixel values close to 1.0 are illustrated in white, while pixel values close to −1.0 are illustrated in black. DSA images are subtraction images acquired by subtracting a mask image which is generated from an X-ray image of an object acquired before the injection of a radiopaque dye, from live images which are X-ray images constituted by a plurality of frames acquired after the injection of the radiopaque dye. Therefore, in an ideal subtraction image, a background region 302 that is acquired by removing a blood vessel region 301 into which the radiopaque dye has been introduced (injected) is cancelled out by subtraction processing, and therefore has a pixel value of 0. The blood vessel region 301 mostly has a pixel value that is far from the pixel value of the background region 302 (a negative pixel value in the example of FIG. 3).

Therefore, with a method of evaluating the states of the injection of the radiopaque dye based on the area of the blood vessel region 301 in DSA images, the number of pixels with negative pixel values is counted. Assume there are DSA moving images with the following conditions: a total number of frames is T, the number of pixel rows in each frame is H, the number of pixel columns in each frame is W, and the $t^{th}$ frame of the DSA moving images is a subtraction image $I_t$ (where $0 \le t < T$). Also assume that a pixel (x, y) in the subtraction image $I_t$ (where $0 \le x < W$, $0 \le y < H$) has a pixel value $I_t(x, y)$. Also assume that a threshold to separate the background region 302 with a pixel value of 0 from the blood vessel region 301 is generalized as thresh. Under the above relationships, an evaluation value $Sv_t$ for the $t^{th}$ frame of the DSA moving images can be expressed by the following equation.

$$Sv_t = \frac{\sum_{y=0}^{y<H} \sum_{x=0}^{x<W} f_t(x, y)}{H \times W}$$ [Expression 1]

$$f_t(x, y) = \begin{cases} 1 & I_t(x, y) < \text{thresh} \\ 0 & I_t(x, y) \geq \text{thresh} \end{cases}$$

In step S202, the evaluation unit 108 outputs the evaluation values to the reference image selection unit 109, and the reference image selection unit 109 selects at least one frame that is suitable as a reference image from the DSA images based on the evaluation values output from the evaluation unit 108.

According to the above-described example, in step S201, the evaluation unit 108 evaluates the states of the injection of the radiopaque dye based on the area of a blood vessel region in the DSA images, and calculates an evaluation value $Sv_t$ as an evaluation value for the $t^{th}$ frame of the DSA moving images (where $0 \leq t < T$).

An image showing the state where the radiopaque dye is widely spread in a blood vessel region is suitable as a reference image. Therefore, the frame $t_{ref}$ selected by the reference image selection unit 109 has the largest evaluation value Sv of all the frames output from the evaluation unit 108. Using an evaluation value output from the evaluation unit 108, the frame $t_{ref}$ can be expressed by the following equation.

$$t_{ref} = \{t \in 0 \leq t < T : Sv_t \underset{0 \leq t < T}{=} \max Sv_t\}$$ [Expression 2]

The above equation indicates that the $t^{th}$ frame with the largest evaluation value $Sv_t$ is selected by the reference image selection unit 109 as the reference image (frame $t_{ref}$). The above equation is applicable under the assumption that the reference image selection unit 109 selects one frame, i.e. the $t^{th}$ frame with the largest evaluation value $Sv_t$ as the reference image (where $0 \leq t < T$). It should be noted, however, that the reference image selection unit 109 is not limited to selecting one frame image as the reference image based on the largest evaluation value Sv. Alternatively, the reference image selection unit 109 may select a plurality of frame images using the evaluation values Sv. For example, in the case where two or more frames are selected as reference images and reproduced one by one in a loop at a predetermined frame rate, a plurality of frames that precede and succeed a frame with the largest evaluation value Sv may be selected. Alternatively, a plurality of frames may be selected in the order of the largest evaluation value Sv to the smallest evaluation value Sv.

In the present embodiment, the evaluation unit 108 evaluates the frames (DSA images) of the DSA moving images based on the area of the blood vessel region in the DSA images, and the reference image selection unit 109 selects (outputs) a frame including a blood vessel region of the largest area as a reference image. By outputting this reference image to the image display unit 110, the problem of frame selection can be alleviated for the operator of the X-ray image processing apparatus.

In the above-described example, pixel values of pixels included in the frames (DSA images) are compared with a threshold, and evaluation values are calculated using the number of pixels with pixel values within a predetermined range. It should be noted, however, that DSA images include minute noise that has pixel values resembling blood vessels filled with a radiopaque dye. In view of this, the evaluation unit 108 may calculate evaluation values in consideration of the continuity of pixels in addition to the number of pixels with pixel values within a predetermined range. For example, the evaluation unit 108 may calculate the number of pixels that have pixel values falling within a predetermined range with respect to a threshold and that are continuously arranged as an evaluation value. As a region of blood vessels filled with a radiopaque dye can be thought as a region that is continuous with the tip of the catheter, the use of evaluation values calculated in the above manner can further improve the accuracy of selection of a reference image.

Regarding the examples of the blood vessel region 301 and the background region 302 illustrated in FIG. 3, the area of the blood vessel region 301 in a DSA image is used as the evaluation value for an ideal subtraction image. However, in an actual subtraction image, a motion artifact 303 could appear due to the movement of the object and the movement of the inserted catheter. For example, the motion artifact 303 has both positive and negative pixel values as illustrated in FIG. 3, and thus has a large influence on the image quality of a DSA image. It is possible that the motion artifact 303 in a reference image be small. In order to select a reference image in consideration of the existence of the motion artifact 303, values associated with the motion artifact 303 may be added to the evaluation values calculated by the evaluation unit 108 in step S201.

There are various methods of calculating evaluation values that take the motion artifact 303 into consideration. Unlike the blood vessel region 301 that mostly has negative pixel values, the motion artifact 303 could have both positive and negative pixel values as illustrated in FIG. 3. For example, the motion artifact 303 could include a region with pixel values close to 1.0 (a white region) and a region with pixel values close to −1.0 (a black region). The following describes a method whereby the number of pixels with positive pixel values is counted as a simple example. Provided that a threshold for separating the background region 302 from the motion artifact 303 is thresh2, an evaluation value $Sm_t$ based on the motion artifact 303 can be expressed by the following equation, using the same signs as those used in Expression 1.

$$Sm_t = \frac{\sum_{y=0}^{y<H} \sum_{x=0}^{x<W} f_t(x, y)}{H \times W}$$ [Expression 3]

$$f_t(x, y) = \begin{cases} 1 & I_t(x, y) > \text{thresh2} \\ 0 & I_t(x, y) \leq \text{thresh2} \end{cases}$$

The result of adding this evaluation value Sm based on the motion artifact 303 and an evaluation value Sv based on the area of the blood vessel region 301 is an evaluation value S (=Sm+Sv) to be ultimately calculated. When an evaluation value Sm based on the motion artifact 303 is used, it is possible that the motion artifact 303 in a reference image be small. In view of this, an evaluation value S calculated as a sum of an evaluation value Sv and an evaluation value Sm is expressed by the following equation, using a coefficient a greater than 0 as a weight for the evaluation value Sv, and a coefficient b smaller than 0 as a weight for the evaluation value Sm.

$$S = a \times Sv + b \times Sm$$

$$(a > 0, b < 0)$$ [Expression 4]

Provided that an evaluation value $S_t$ is an evaluation value for the $t^{th}$ frame of the DSA moving images (where $0 \leq t < T$), the frame $t_{ref}$ selected by the reference image selection unit 109 in step S202 can be expressed by the following equation.

$$t_{ref} = \left\{ t \in 0 \leq t < T : S_t \underset{0 \leq t < T}{=} \max S_t \right\} \quad \text{[Expression 5]}$$

Similarly to Expression 2, the above equation indicates that the $t^{th}$ frame with the largest evaluation value $S_t$ is selected by the reference image selection unit 109 as the reference image ($t_{ref}$). That is to say, the reference image selection unit 109 selects a frame including a blood vessel region of a large area and a small motion artifact as a reference image.

The number of pixels at the boundary between the radiopaque dye and the background region may be used to calculate an evaluation value. The boundary between the radiopaque dye and the background region can be determined, for example, by applying edge detection processing to a subtraction image using the Canny edge detector and the like and finding out pixel values at the detected edge positions. By calculating an evaluation value using the number of pixels at the boundary, the complexity of structures of fine blood vessels that cannot be evaluated based only on the aforementioned area of the blood vessel region can be added to the evaluation value, thereby enabling selection of a more suitable reference image.

Furthermore, the evaluation unit 108 can calculate evaluation values based on an imaging portion for which the DSA moving images have been captured, imaging technique information, imaging conditions, and a time period that has elapsed since the injection of the radiopaque dye. A DSA image acquired at the timing when the radiopaque dye has spread throughout the object is selected as a reference image. Therefore, there is a high possibility that a DSA image acquired immediately after the injection of the radiopaque dye, or acquired after a long time period has elapsed since the injection of the radiopaque dye, cannot be used as a reference image. For example, assume that the administered dosage of radiopaque dye determined by the imaging portion and the imaging technique information is Q, the velocity of blood flow in the imaging portion is D, and a frame rate determined by the imaging conditions is R. A range of frames [$t_{start}$, $t_{end}$] that can be used as a reference image when the above conditions are changed is experimentally acquired and stored as a table in advance.

$$\text{table}(Q, D, R) = [t_{start}, t_{end}] \quad \text{[Expression 6]}$$

During the actual imaging, the evaluation unit 108 acquires a frame range [$t_{start}$, $t_{end}$] determined by the imaging conditions from this table, and calculates evaluation values $S_t$ within this frame range. The reference image selection unit 109 then selects the frame $t_{ref}$ as a reference image based on the evaluation values calculated by the evaluation unit 108. With this configuration, a range of frame search can be restricted, and therefore the speed of processing can be accelerated. Note that data stored in the table is not limited to the range of frames that can be used as a reference image. For example, the table may store values from 0.0 to 1.0 as weights $w_t$ corresponding to different sets of the administered dosage Q of radiopaque dye, the velocity D of blood flow in the imaging portion and the frame rate R determined by the imaging conditions. For example, once the administered dosage Q of radiopaque dye, the velocity D of blood flow and the frame rate R have been determined, a corresponding weight $w_t$ can be acquired as shown in the following equation.

$$\text{table}(Q, D, R) = w_t \quad \text{[Expression 7]}$$

Using this weight $w_t$, the frame $t_{ref}$ selected by the reference image selection unit 109 in step S202 can be expressed by the following equation.

$$t_{ref} = \left\{ t \in 0 \leq t < T : w_t \times S_t = \max_{0 \leq t < T} (w_t \times S_t) \right\} \quad \text{[Expression 8]}$$

With the above configuration, a weight is applied to the evaluation value $S_t$ for each frame in correspondence with the administered dosage Q of radiopaque dye, the velocity D of blood flow and the frame rate R, and therefore a reference image can be selected at higher accuracy.

An evaluation value may be the result of comparing a minimum-value projection image M generated from the DSA moving images with the frames of the DSA moving images. Provided that each frame of the DSA moving images is $I_t$ and a value of each pixel therein (x, y) is $I_t(x, y)$, the minimum-value projection image M is expressed by the following equation.

$$M(x, y) = \min_{0 \leq t < T} I_t(x, y) \quad \text{[Expression 9]}$$

Figure 4:
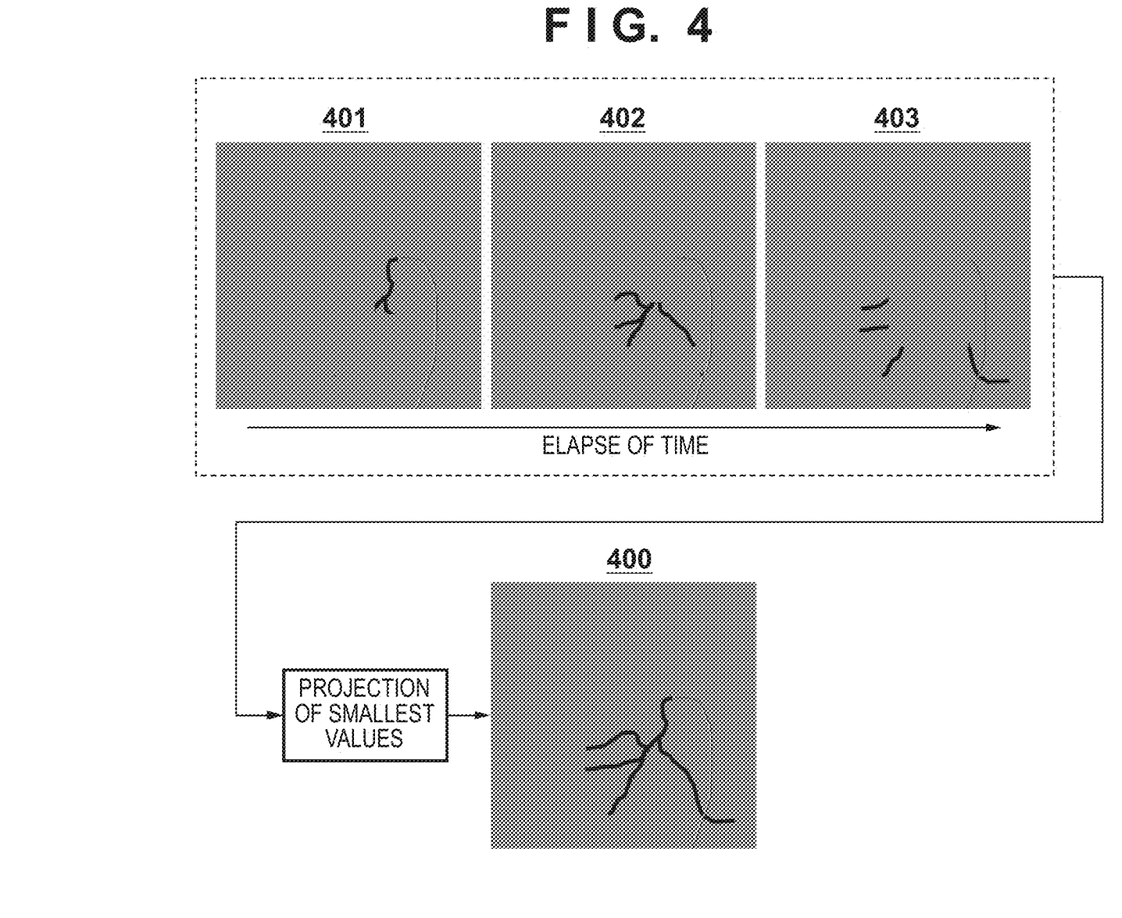
FIG. 4 schematically illustrates a minimum-value projection image.

The pixel value M (x, y) of each pixel (x, y) in the minimum-value projection image M is the smallest of pixel values of corresponding pixels in all the frames of the DSA moving images. FIG. 4 schematically illustrates a minimum-value projection image 400 generated from DSA images 401, 402 and 403. As illustrated in FIG. 4, the position where the region of blood vessels filled with the radiopaque dye is shown changes over time in the DSA images 401, 402 and 403 that are included among the DSA moving images as frames. Therefore, in any of these DSA images (frames), only a part of the entire blood vessel region is shown. The minimum-value projection image 400 constituted by these frames is generated by acquiring pixels that each have the smallest pixel value among corresponding pixels in all the frames. When any of the frames constituting the DSA moving images includes the region of blood vessels filled with the radiopaque dye, pixel values of this region of blood vessels filled with the radiopaque dye are acquired as the minimum pixel values. Therefore, the minimum-value projection image 400 can show the entire blood vessel region. Evaluation values $Sc_t$ based on comparison between this minimum-value projection image M and the frames of the DSA moving images can be calculated using the following equation.

$$Sc_t = \sum_{y=0}^{y<H} \sum_{x=0}^{x \leq W} |I_t(x, y) - M(x, y)| \quad \text{[Expression 10]}$$

The smallest evaluation value $Sc_t$ is acquired from a frame of the DSA moving images that is closest to the minimum-value projection image M, that is to say, a frame of the DSA moving images in which the radiopaque dye has spread over a wide range. In view of this, by adding the result of multiplication by a predetermined coefficient smaller than 0 to the evaluation value in a manner similar to the evaluation value Sm based on the motion artifact, a more suitable reference image can be selected.

Although several types of calculation of evaluation values have been described above as examples, evaluation values that can be used in the present invention are not limited to the above examples. For example, the evaluation unit 108 may calculate evaluation values based on the addition of a plurality of feature amounts calculated from the frames of the subtraction images. For example, provided that an evaluation value S is acquired by calculating n types of feature amounts ($S_1$, $S_2$, . . . , $S_n$) from an image I and adding the feature amounts multiplied by weight coefficients ($k_1$, $k_2$, . . . , $k_n$) through linear combination, the evaluation value S can be expressed by the following equation.

$$S = k_1 \times S_1 + k_2 \times S_2 + \ldots + k_n \times S_n \quad \text{[Expression 11]}$$

The value of each weight coefficient k is, for example, larger than 0 when the corresponding feature amount is large and represents a reference image (S>0), and smaller than 0 when the corresponding feature amount is small and represents a reference image (S<0).

In this case, the reference image selection unit 109 can select a reference image based on a plurality of feature amounts by selecting a frame in accordance with the evaluation values S (e.g. a frame with the largest evaluation value S).

Figure 1:
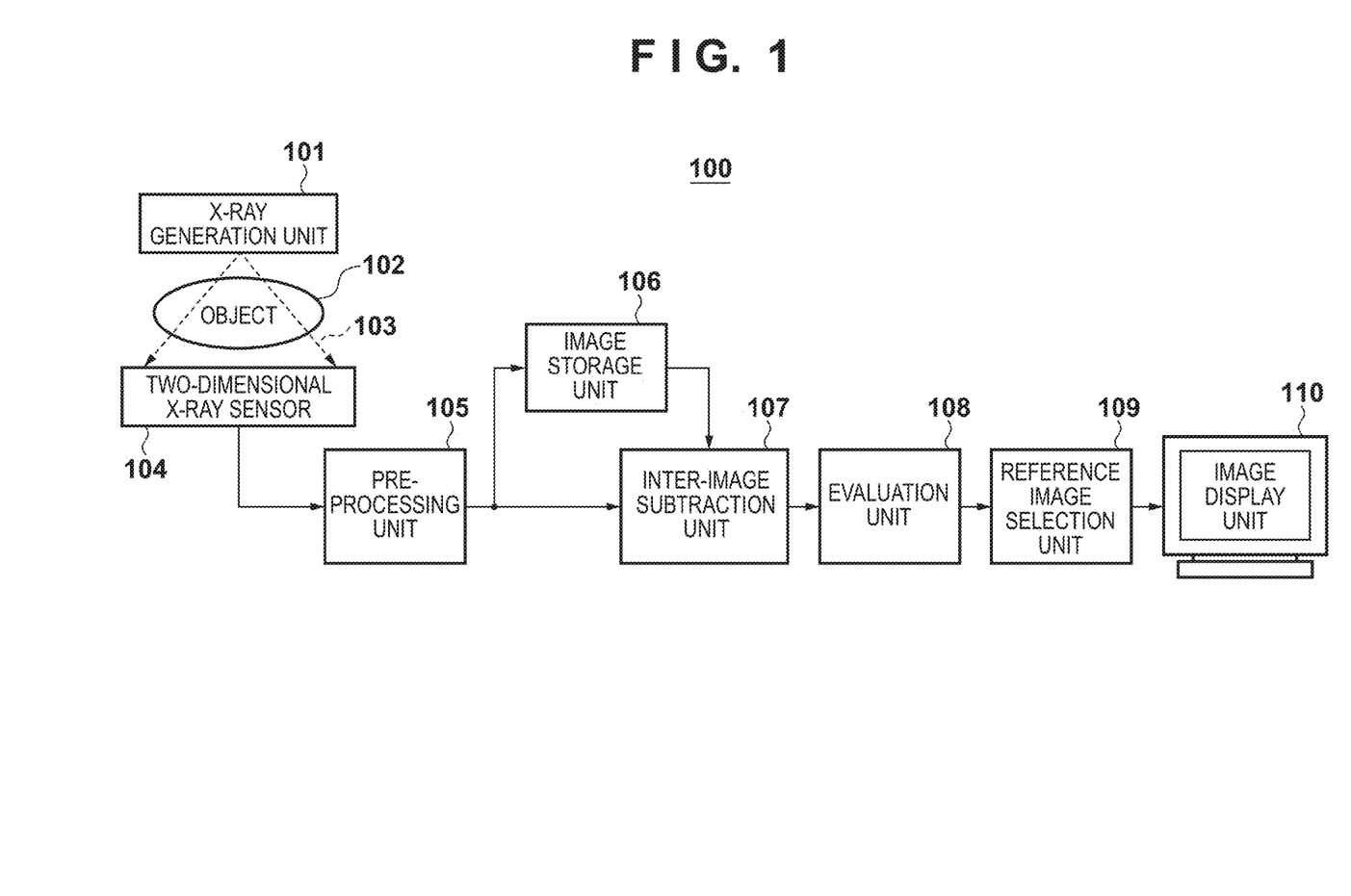
FIG. 1 illustrates a configuration of an image processing apparatus according to an embodiment.

The components illustrated in FIG. 1 may be configured by special-purpose hardware. Functional configurations of the hardware may be realized by software. In this case, the functions of the components illustrated in FIG. 1 may be realized by installing software on an information processing apparatus and implementing an image processing method through the execution of the software using the arithmetic functions of the information processing apparatus. For example, through the execution of the software, a subtraction step, an evaluation step and a selection step are executed for the frames of the moving images output from the two-dimensional X-ray sensor 104.

Figure 5:
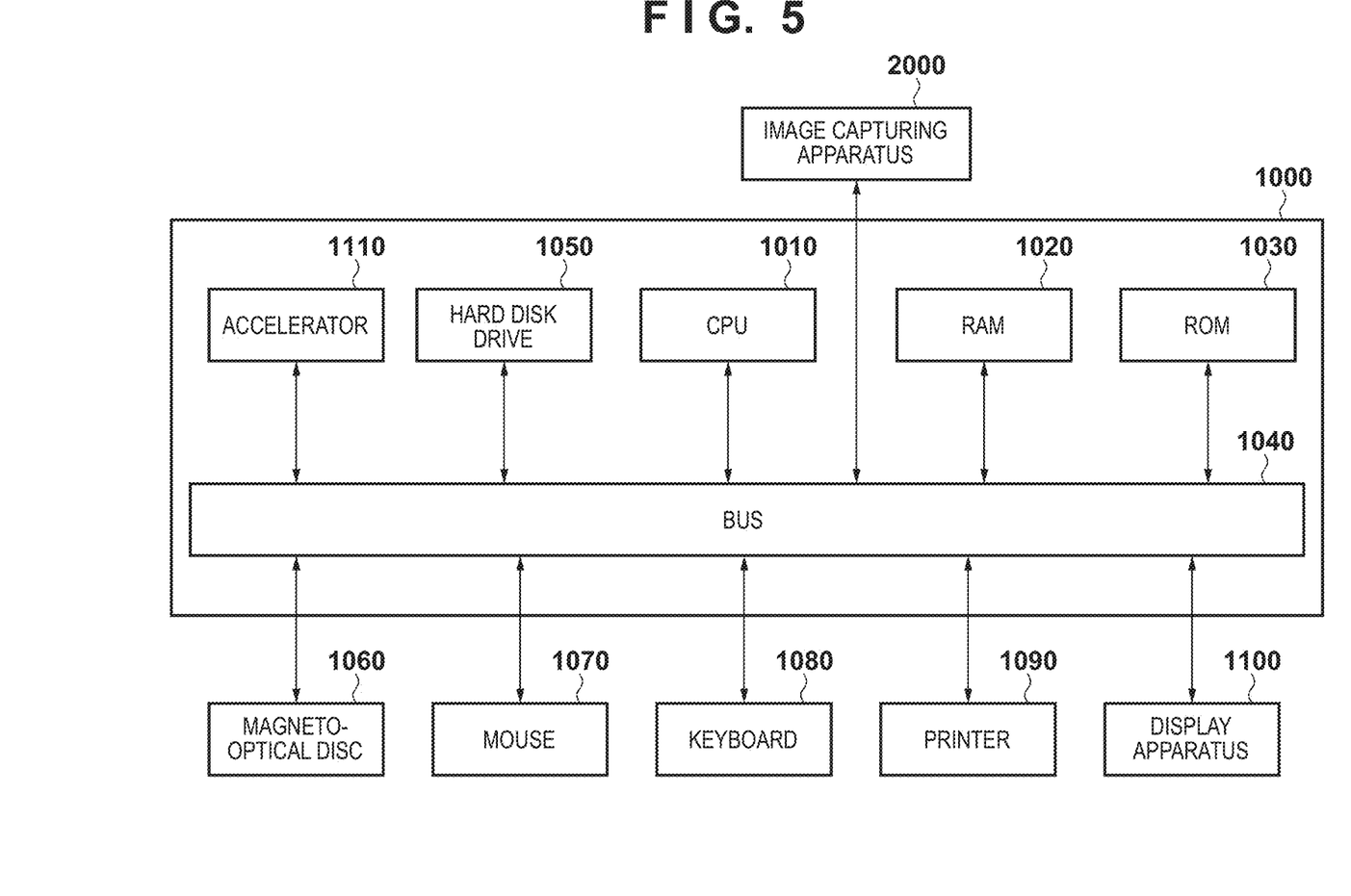
FIG. 5 illustrates a configuration of an information processing apparatus according to an embodiment.

FIG. 5 is a block diagram illustrating a hardware configuration of an information processing apparatus and configurations of peripheral apparatuses therefor. An information processing apparatus 1000 and an image capturing apparatus 2000 are connected to each other and are configured to perform data communication with each other.

(Information Processing Apparatus)

A CPU 1010 can control the entirety of the information processing apparatus 1000 using programs and data stored in a RAM 1020 and a ROM 1030. The CPU 1010 can also execute arithmetic processing related to predetermined image processing by executing programs.

The RAM 1020 includes an area for temporarily storing programs and data loaded from a magneto-optical disc 1060 and a hard disk drive 1050. The RAM 1020 also includes an area for temporarily storing data of X-ray fluoroscopy moving images acquired from the image capturing apparatus 2000. The RAM 1020 also includes a work area used when the CPU 1010 executes various types of processing.

The ROM 1030 stores data of the settings of the information processing apparatus 1000, boot programs, and the like.

The hard disk drive 1050 is one example of an information storage medium, and stores programs and data for causing the CPU 1010 to execute processing of an operating system (OS) and the components illustrated in FIG. 1. They are loaded to the RAM 1020 as appropriate in accordance with control by the CPU 1010 and are executed by the CPU 1010. Data of the X-ray fluoroscopy moving images may also be stored in the hard disk drive 1050.

The magneto-optical disc 1060 is one example of an information storage medium, and can store a part or all of the programs and data stored in the hard disk drive 1050.

A mouse 1070 and a keyboard 1080 can input various types of instructions to the CPU 1010 by being operated by an operator of the information processing apparatus 1000.

A printer 1090 can print/output images displayed on the image display unit 110 on/to a recording medium.

A display apparatus 1100 is constituted by a CRT, a liquid crystal display, or the like, and can display the result of processing of the CPU 1010 using images and text. For example, the display apparatus 1100 can display images that have been processed by the components illustrated in FIG. 1 and ultimately output from the image display unit 110. In this case, the image display unit 110 functions as a display control unit for displaying images on the display apparatus 1100. A bus 1040, which connects between the components of the information processing apparatus 1000, enables them to exchange data with one another.

(Image Capturing Apparatus)

A description is now given of the image capturing apparatus 2000. The image capturing apparatus 2000 is an apparatus that can capture moving images, such as an X-ray fluoroscope. The image capturing apparatus 2000 transmits captured image data to the information processing apparatus 1000. Note that the image capturing apparatus 2000 may transmit a plurality of pieces of image data collectively to the information processing apparatus 1000, or may transmit a piece of image data each time it captures an image.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-106311, filed May 7, 2012, which is hereby incorporated by reference herein in its entirety.

What is claimed is:

1. An image processing apparatus comprising:
    a subtraction unit configured to generate a digital subtraction angiography moving image composed of a plurality of frames, from X-ray images of an object acquired before and after injecting a radiopaque dye into the object;
    an evaluation unit configured to calculate evaluation values for each of the plurality of frames of the digital subtraction angiography moving image;
    a selection unit configured to select, by comparing the evaluation values for each of the plurality of frames, at least one frame from the plurality of frames of the digital subtraction angiography moving image; and
    an output unit configured to output the selected frame as a reference image.

2. The image processing apparatus according to claim 1, wherein the subtraction unit is configured to generate each of the plurality of frames of the digital subtraction angiography moving image by subtracting a mask image from live images, the mask image being generated from an X-ray image of the object acquired before injecting the radiopaque dye, and the live images being X-ray images constituted by a plurality of frames acquired after injection of the radiopaque dye.

3. The image processing apparatus according to claim 1, wherein the evaluation unit is configured to calculate the evaluation values from the plurality of frames of the digital subtraction angiography moving image using the number of pixels that have pixel values falling within a predetermined range with respect to a threshold.

4. The image processing apparatus according to claim 3, wherein the evaluation unit is configured to calculate the evaluation values from the plurality of frames of the digital subtraction angiography moving image using the number of pixels that have pixel values falling within a predetermined range with respect to a threshold and that are continuously arranged.

5. The image processing apparatus according to claim 1, wherein the evaluation unit is configured to calculate the evaluation values from the plurality of frames of the digital subtraction angiography moving image using the number of pixels at a boundary between the radiopaque dye and a background region.

6. The image processing apparatus according to claim 1, wherein the evaluation unit is configured to calculate the evaluation values based on an imaging portion for which the plurality of frames of the digital subtraction angiography moving image have been generated, imaging technique information, imaging conditions, and a time period that has elapsed since the injection of the radiopaque dye.

7. The image processing apparatus according to claim 6, wherein the evaluation unit is configured to acquire a frame range for the plurality of frames of the digital subtraction angiography moving image based on the imaging conditions and to calculate the evaluation values within the frame range.

8. The image processing apparatus according to claim 1, wherein the evaluation unit is configured to calculate the evaluation values by comparing a minimum-value projection image with the plurality of frames of the digital subtraction angiography moving image, the minimum-value projection image being constituted by pixels that each have the smallest pixel value among corresponding pixels in all the plurality of frames of the digital subtraction angiography moving image.

9. The image processing apparatus according to claim 1, wherein the evaluation unit is configured to calculate a plurality of feature amounts from the plurality of frames of the digital subtraction angiography moving image, and to calculate the evaluation values based on addition of the calculated plurality of feature amounts.

10. The image processing apparatus according to claim 9, wherein the evaluation unit is configured to calculate the evaluation values by adding values acquired by multiplying the plurality of feature amounts calculated from the plurality of frames of the digital subtraction angiography moving image by weight coefficients through linear combination.

11. The image processing apparatus according to claim 1, further comprising an image display unit configured to display the reference image.

12. The image processing apparatus according to claim 11, wherein the selection unit is configured to select, using the evaluation values, more than one of the plurality of frames as reference images, and wherein the image display unit is configured such that when a plurality of frames have been selected as reference images, the image display unit displays the reference images one by one at a predetermined frame rate.

13. The image processing apparatus according to claim 1, further comprising a storage unit configured to store the reference image.

14. An image processing method for an image processing apparatus, said method comprising:
- a subtraction step of generating a digital subtraction angiography moving image composed of a plurality of frames, from X-ray images of an object acquired before and after injecting a radiopaque dye into the object;
- an evaluation step of calculating evaluation values for each of the plurality of frames of the digital subtraction angiography moving image;
- a selection step of selecting, by comparing the evaluation values for each of the plurality of frames, at least one frame from the plurality of frames of the digital subtraction angiography moving image; and
- an outputting step of outputting the selected frame one of the frames as a reference image.

15. A non-transitory computer readable storage medium having stored therein a program for causing a computer to execute an image processing method for an image processing apparatus, said method comprising:
- a subtraction step of generating a digital subtraction angiography moving image composed of a plurality of frames, from X-ray images of an object acquired before and after injecting a radiopaque dye into the object;
- an evaluation step of calculating evaluation values for each of the plurality of frames of the digital subtraction angiography moving image;
- a selection step of selecting, by comparing using the evaluation values for each of the plurality of frames, at least one frame from the plurality of frames of the digital subtraction angiography moving image; and
- an outputting step of outputting the selected frame as a reference image.

16. The image processing apparatus according to claim 1, wherein the evaluation unit calculates the evaluation values by evaluating states of injection of the radiopaque dye for the plurality of frames of the digital subtraction angiography moving image.

17. The image processing apparatus according to claim 1, wherein the evaluation unit evaluates a blood vessel region for each of the plurality of frames of the digital subtraction angiography moving image.

18. The image processing apparatus according to claim 17, wherein the selection unit selects, as the reference image, a frame including a blood vessel region of a largest area among the plurality of frames.

* * * * *